United States Patent
Jung et al.

(10) Patent No.: US 11,633,157 B2
(45) Date of Patent: Apr. 25, 2023

(54) PHOTOPLETHYSMOGRAM (PPG) SENSING MODULE AND DEVICE INCLUDING THE SAME

(71) Applicant: SAMSUNG ELECTRONICS CO., LTD., Suwon-si (KR)

(72) Inventors: Sungjin Jung, Hwaseong-si (KR); Jongboo Kim, Seongnam-si (KR); Jeongho Park, Seoul (KR); Long Yan, Hwaseong-si (KR); Seoungjae Yoo, Seongnam-si (KR); Yuncheol Han, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 317 days.

(21) Appl. No.: 17/024,903

(22) Filed: Sep. 18, 2020

(65) Prior Publication Data
US 2021/0186431 A1    Jun. 24, 2021

(30) Foreign Application Priority Data

Dec. 20, 2019   (KR) .................. 10-2019-0171582

(51) Int. Cl.
*A61B 5/00*     (2006.01)
*A61B 5/024*    (2006.01)

(52) U.S. Cl.
CPC ........ *A61B 5/7214* (2013.01); *A61B 5/02416* (2013.01); *A61B 5/7225* (2013.01)

(58) Field of Classification Search
CPC ... A61B 5/02416; A61B 5/681; A61B 5/6898; A61B 5/70; A61B 5/7207; A61B 5/7214; A61B 5/7225; A61B 5/7264
See application file for complete search history.

(56) References Cited

U.S. PATENT DOCUMENTS

| | | | |
|---|---|---|---|
| 2015/0190062 A1* | 7/2015 | Han | A61B 5/11 600/479 |
| 2016/0022220 A1* | 1/2016 | Lee | A61B 5/02433 600/479 |
| 2018/0000359 A1 | 1/2018 | Watanabe | |

FOREIGN PATENT DOCUMENTS

| | | |
|---|---|---|
| JP | 2017-314 A | 1/2017 |
| JP | 2017-140202 A | 8/2017 |
| JP | 2018-8039 A | 1/2018 |
| KR | 10-0849667 B1 | 8/2008 |
| KR | 10-0963253 B1 | 6/2010 |
| KR | 10-1038432 B1 | 6/2011 |

(Continued)

*Primary Examiner* — Mark D Remaly
(74) *Attorney, Agent, or Firm* — Sughrue Mion, PLLC

(57) ABSTRACT

Provided is a photoplethysmogram (PPG) sensing module including one or more light sources that emit light to a user; a plurality of optical sensors that receive reflected light from the user and generate sensing signals, each of the sensing signals being generated by one of the optical sensors; a read-out signal generating circuit that receives the sensing signals from the optical sensors and generate read-out signals by performing an analog-to-digital conversion on the sensing signals; and a signal processing circuit that receives the read-out signals, classifies the read-out signals according to one or more movement patterns of the user, measures a movement component of the user based on the classified read-out signals, and generates a PPG signal in which the movement component is removed.

20 Claims, 16 Drawing Sheets

(56) References Cited

FOREIGN PATENT DOCUMENTS

| KR | 10-2019-0074463 A | 6/2019 |
|---|---|---|
| KR | 10-1978552 B1 | 8/2019 |

* cited by examiner

PHOTOPLETHYSMOGRAM (PPG) SENSING MODULE AND DEVICE INCLUDING THE SAME

CROSS-REFERENCE TO THE RELATED APPLICATIONS

This application is based on and claims priority from Korean Patent Application No. 10-2019-0171582, filed on Dec. 20, 2019, in the Korean Intellectual Property Office, the disclosure of which is incorporated herein in its entirety by reference.

BACKGROUND

1 Field

The inventive concept relates to a Photoplethysmogram (PPG) sensing module, and more particularly, to a PPG sensing module capable of accurately sensing a user's heart rate and a device including the same.

2. DESCRIPTION OF RELATED ART

In the field of sensing technology, because a light absorption coefficient of a blood vessel changes according to change of a heart rate, a heart rate sensor module may be synchronized with a heart rate of a user (or a subject) and measure a heart rate or blood oxygen saturation by irradiating light on the skin of the user and sensing reflected light. However, when a separation occurs between the heart rate sensor module and the skin due to a movement of the user, a reflection coefficient is changed and distortion may occur in a reflected optical signal. As a result, the accuracy of a heart rate and blood oxygen saturation may be deteriorated.

To address the problem above, a separate acceleration sensor and a gyro sensor are used to measure a movement of a user. However, this may cause difficulties like cost increase, area increase, and power consumption increase of a PPG sensing module.

SUMMARY

The inventive concept provides a PPG sensing module capable of accurately sensing a PPG of a user by detecting a movement of a user and providing a sensing result to the user so as to inform the user his/her accurate biometric information and an apparatus including the PPG sensing module.

According to an aspect of the inventive concept, there is provided a photoplethysmogram (PPG) sensing module comprising: one or more light sources configured to emit light on a user; a plurality of optical sensors configured to receive reflected light from the user and generate a plurality of sensing signals, each of the plurality of sensing signals being generated by one of the plurality of optical sensors; a read-out signal generating circuit configured to receive the plurality of sensing signals from the plurality of optical sensors and generate a plurality of read-out signals by performing an analog-to-digital conversion on the plurality of sensing signals; and a signal processing circuit configured to: receive the plurality of read-out signals, classify the plurality of read-out signals according to one or more movement patterns of the user, measure a movement component of the user based on the classified plurality of read-out signals, and generate a PPG signal in which the movement component is removed.

According to another aspect of the inventive concept, there is provided a PPG sensing chip comprising: a plurality of optical sensors configured to receive light from a user and generate a plurality of sensing signals, each of the plurality of sensing signals being generated by one of the plurality of optical sensors; a read-out signal generating circuit configured to receive the plurality of sensing signals from the plurality of optical sensors and generate a plurality of read-out signals by performing an analog-to-digital conversion operation on the plurality of sensing signals; and a signal processing circuit configured to: receive the plurality of read-out signals, generate a PPG signal by using the plurality of read-out signals, measure a movement component of the user based on position information of the plurality of optical sensors, and remove the movement component from the PPG signal.

According to another aspect of the inventive concept, there is provided an apparatus comprising: a PPG sensing module; and an output unit configured to output PPG signal-related information generated by the PPG sensing module to a user, wherein the PPG sensing module comprises: one or more light sources configured to emit light on a user; a plurality of optical sensors configured to receive reflected light from the user and generate a plurality of sensing signals, each of the plurality of sensing signals being generated by one of the plurality of optical sensors; a read-out signal generating circuit configured to receive the plurality of sensing signals from the plurality of optical sensors and generate a plurality of read-out signals by performing an analog-to-digital conversion on the plurality of sensing signals; and a signal processing circuit configured to: receive the plurality of read-out signals, measure a movement component of the user based on the plurality of read-out signals, and generate the PPG signal from which the movement component is removed.

According to another aspect of the inventive concept, there is provided an apparatus comprising: a memory storing one or more instructions; and a processor configured to execute the one or more instructions to: receive a plurality of read-out signals generated based on reflected light from a user that is detected by a plurality of optical sensors, classify the plurality of read-out signals according to one or more movement patterns of the user, measure a movement component of the user based on the classified plurality of read-out signals, and generate a PPG signal in which the movement component is removed.

BRIEF DESCRIPTION OF THE DRAWINGS

Embodiments of the inventive concept will be more clearly understood from the following detailed description taken in conjunction with the accompanying drawings in which.

DETAILED DESCRIPTION OF THE EMBODIMENTS

Figure 1:
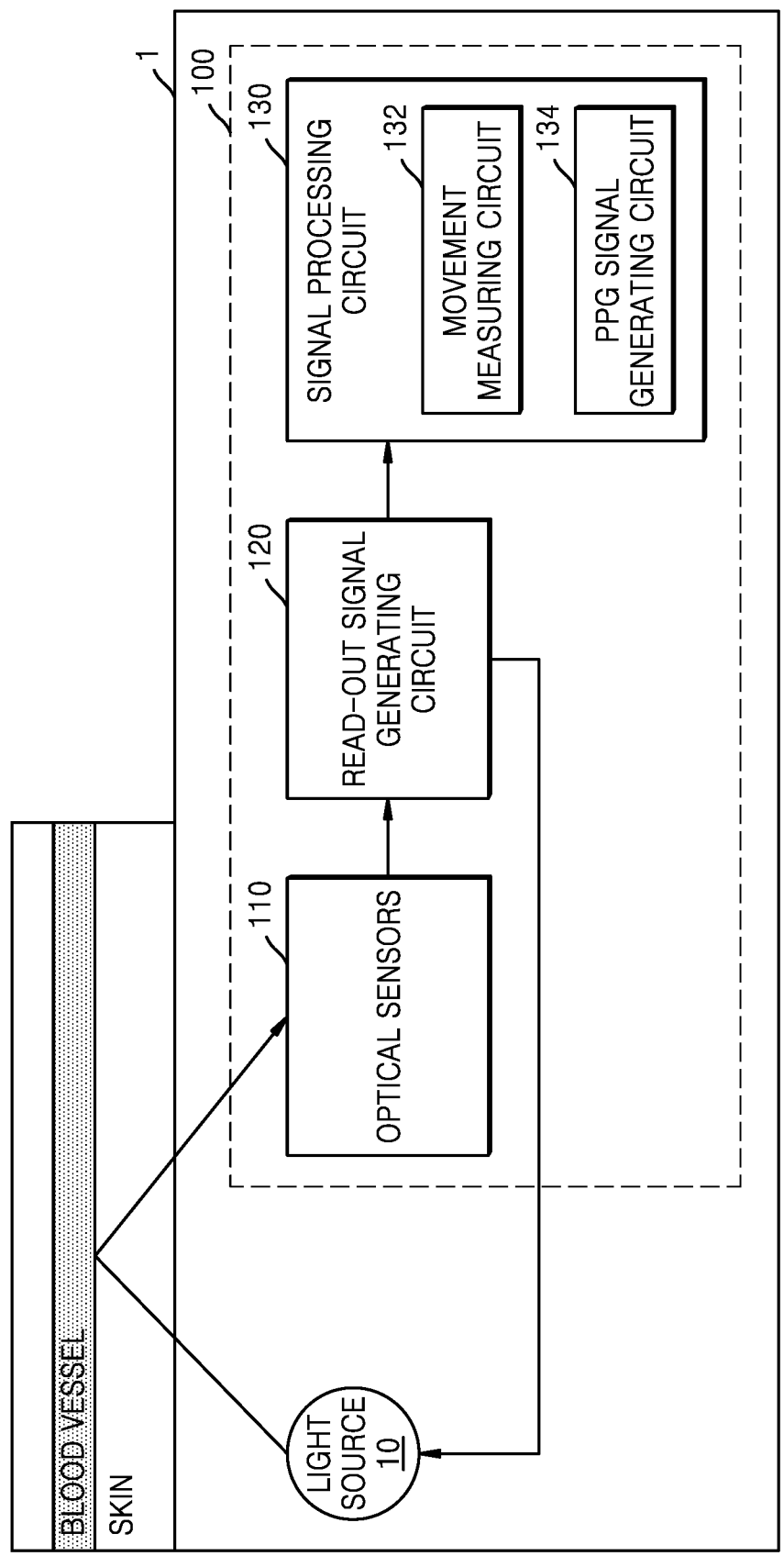
FIG. 1 is a block diagram showing a PPG sensing module according to an example embodiment of the inventive concept.

FIG. 1 is a block diagram showing a photoplethysmogram (PPG) sensing module 1 according to an example embodiment of the inventive concept.

Referring to FIG. 1, the PPG sensing module 1 may include a light source 10 and a PPG sensing chip 100. The PPG sensing chip 100 may include a plurality of optical sensors 110, a read-out signal generating circuit 120, and a signal processing circuit 130. The PPG sensing chip 100 may sense a PPG signal (or a heart rate signal) and may further sense biometric signals like an electrocardiography (ECG) signal and an electromyography (EMG) signal. Hereinafter, example embodiments of the PPG sensing module 1 for sensing a movement of a user (or a subject) while sensing a PPG signal are described. However, the inventive concept is not limited thereto and may be applied to sensing of other biometric signals.

The light source 10 may emit light to a certain portion of a user to sense a PPG signal of the user. The portion of the user to which light is irradiated may vary, and for convenience of explanation, the portion of the user to which light is irradiated may be hereinafter collectively referred to as the user. For example, the light source 10 may emit light to the user's skin that corresponds to a location at which capillary blood, arterial blood, or venous blood of the user flows. The light source 10 may be implemented with a light emitting diode (LED), a laser diode (LD), or a phosphor. However, it is merely an example embodiment and is not limited thereto. The light source 10 may be replaced with a plurality of light sources, wherein the plurality of light sources may emit light having different wavelengths, respectively.

The optical sensors 110 may generate sensing signals by receiving light irradiated on the skin from the light source 10 and scattered or reflected from a blood vessel. The optical sensors 110 may be implemented with a photodiode, a phototransistor, or an image sensor (e.g., a CMOS image sensor). Also, the optical sensors 110 may be implemented with electronic circuitry. The optical sensors 110 may be arranged in various ways to generate a PPG signal of a user and sensing signals needed to detect movements of the user. The arrangement of the optical sensors 110 will be described in detail below with reference to FIGS. 3A to 3D.

The read-out signal generating circuit 120 may receive sensing signals from the optical sensors 110, and generate a plurality of read-out signals. According to an example embodiment, the read-out signal generating circuit 120 may convert the sensing signals, which are received from the optical sensors 110, from analog signals to digital signals. The read-out signal generating circuit 120 according to an example embodiment may include one read-out circuit or a plurality of read-out circuits to generate sensing signals respectively from the optical sensors 110, and the configuration and the operation thereof will be described in detail below with reference to FIGS. 4 and 6. Moreover, the read-out signal generating circuit 120 may control ON/OFF of the light source 10. According to an example embodiment, the read-out signal generating circuit 120 may control the light source 10 to measure movement components of a user. For example, the read-out signal generating circuit 120 may control the light source 10 to switch ON and OFF to measure the movement of the user. However, the control scheme of the read-out signal generating circuit 120 may vary depending on the implementation examples of the read-out signal generating circuit 120.

In a case when a user moves while a PPG signal is being sensed, the optical sensors 110 and the skin may be detached from each other due to the movement, and as a result, factors such the reflection coefficient of a blood vessel may be changed. Accordingly, light received by the optical sensors 110 may be distorted, and this distortion of the light may be included in read-out signals generated by the read-out signal generating circuit 120.

The signal processing circuit 130 according to an example embodiment may include a movement measuring circuit 132 and a PPG signal generating circuit 134. The movement measuring circuit 132 may classify the read-out signals in order to consider patterns to identify that the user may be moving and measure movement components of the user by using the classified read-out signals. According to an example embodiment, there may be various moving patterns associated with the user's movement, and therefore a certain signal processing process may be repeatedly performed to detect the various moving patterns. In other words, the movement measuring circuit 132 may detect movement patterns of a user by using read-out signals and measure the movement component according to the movement patterns.

The PPG signal generating circuit 134 according to an example embodiment may generate a PPG signal by using read-out signals and remove measured movement components measured by the movement measuring circuit 132 from the PPG signal. Accordingly, the PPG signal generating circuit 134 may generate an accurate PPG signal without the distortion or noise from the movement of the user.

The PPG sensing module 1 according to an example embodiment of the inventive concept may measure movement components of a user by using sensing signals generated through the optical sensors 110 and may generate an accurate PPG signal without movement components, thereby providing an accurate PPG signal to the user. Also, because the PPG sensing module 1 may measure movement components of a user by using optical sensors, a separate acceleration sensor, a gyro sensor, or the like is not needed, and thus, cost reduction, design area availability, and power consumption may be improved.

Figure 2:
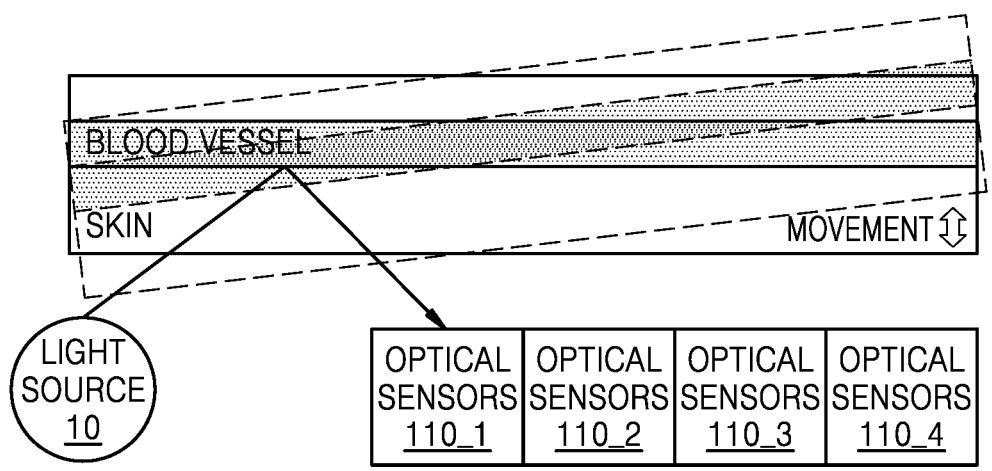
FIG. 2 is a diagram for describing an example of the arrangement of optical sensors of FIG. 1.

FIG. 2 is a diagram for describing an example of the arrangement of the optical sensors 110 of FIG. 1.

Referring to FIG. 2, optical sensors 110_1 to 110_4 may be variously arranged inside the PPG sensing module 1, as illustrated in FIG. 1, to be in contact with or positioned within a certain distance from the skin of a user. For example, the optical sensors 110_1 to 110_4 may be arranged linearly in one direction, and the optical sensors 110_1 to 110_4 may each be located within a certain distance from the skin. According to use case, the position of a blood vessel that reflects light emitted from the light source 10 may be changed due to a movement of a user, and thus, light received by the optical sensors 110_1 to 110_4 may be distorted.

According to an example embodiment, position information may be allocated respectively to each of the optical sensors 110_1 to 110_4 to measure movement components according to movement patterns, and sensing signals generated by the optical sensors 110_1 to 110_4 may be processed based on the position information. The optical sensors 110_1 to 110_4 may be variously arranged or aligned according to the type of a device in which the PPG sensing module 1 of FIG. 1 is included, to accurately measure movement components and a PPG signal.

FIGS. 3A to 3D are diagrams showing arrangement examples of the optical sensors 110 of FIG. 1.

Figure 3A:
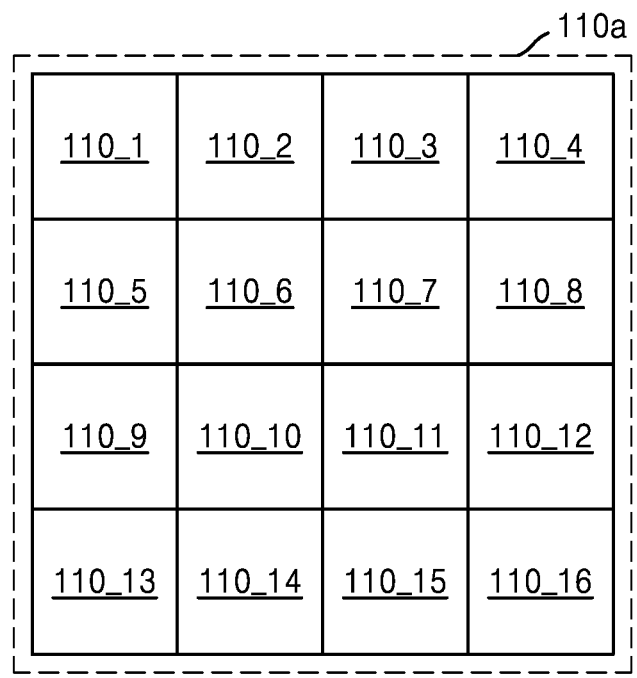
FIGS. 3A to 3D are diagrams showing arrangement examples of the optical sensors of FIG. 1.

Referring to FIG. 3A, optical sensors 110a may include first to sixteenth optical sensors 110_1 to 110_16. The first to sixteenth optical sensors 110_1 to 110_16 may be aligned and arranged in a 4×4 square shape. However, FIG. 3A is merely an embodiment, and the inventive concept is not limited thereto. For instance, the number of optical sensors may by more than sixteen or fewer than sixteen, and these optical sensors may be aligned and arranged in n×n square shapes. According to an example embodiment, the sensors may be arranged in shape different that a square shape.

Figure 3B:
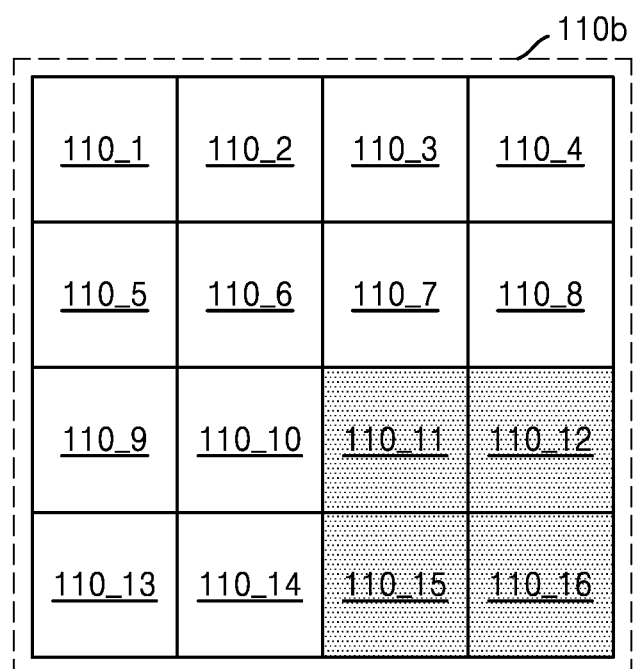

Referring to FIG. 3B, optical sensors 110b may include first optical sensors 110_1 to 110_8, 110_9, 110_10, 110_13, and 110_14 for generating sensing signals for generating a PPG signal and second optical sensors 110_11, 110_12, 110_15, and 110_16 for generating the sensing signals for measuring movement components of a user. In other words, the optical sensors 110b may include dedicated optical sensors configured to generate a PPG signal and dedicated optical sensors configured to measure movement components.

The second optical sensors 110_11, 110_12, 110_15, and 110_16 may be arranged in a certain region, adjacent to one another. The region where the second optical sensors 110_11, 110_12, 110_15, and 110_16 are arranged may correspond to a region where a space between the skin of a user and the PPG sensing module 1 that are separated from each other due to a movement of the user is expected to be or above a critical level. In some embodiments, sensing signals generated by the second optical sensors 110_11, 110_12, 110_15, and 110_16 may also be used to generate a PPG signal.

Figure 3C:
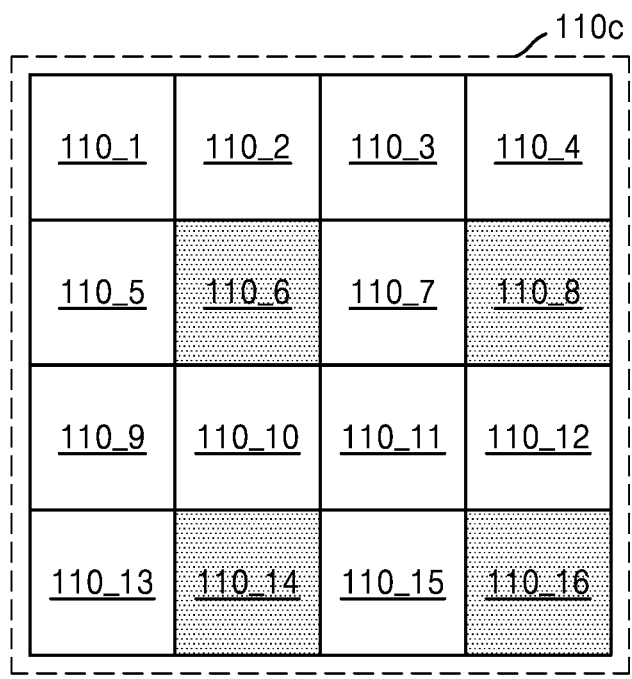

Referring to FIG. 3C, optical sensors 110c may include first optical sensors 110_1 to 110_4, 110_5, 110_7, 110_9 to 110_12, 110_13, and 110_15 for generating sensing signals for measuring a PPG signal and second optical sensors 110_6, 110_8, 110_14, and 110_16 for generating the sensing signals for measuring movement components of a user. The second optical sensors 110_6, 110_8, 110_14, and 110_16 may be a certain distance apart from one another and interspersed between the first optical sensors 110_1 to 110_4, 110_5, 110_7, 110_9 to 110_12, 110_13, and 110_15.

In some embodiments, sensing signals generated by the second optical sensors 110_6, 110_8, 110_14, and 110_16 may also be used to measure a PPG signal.

Figure 3D:
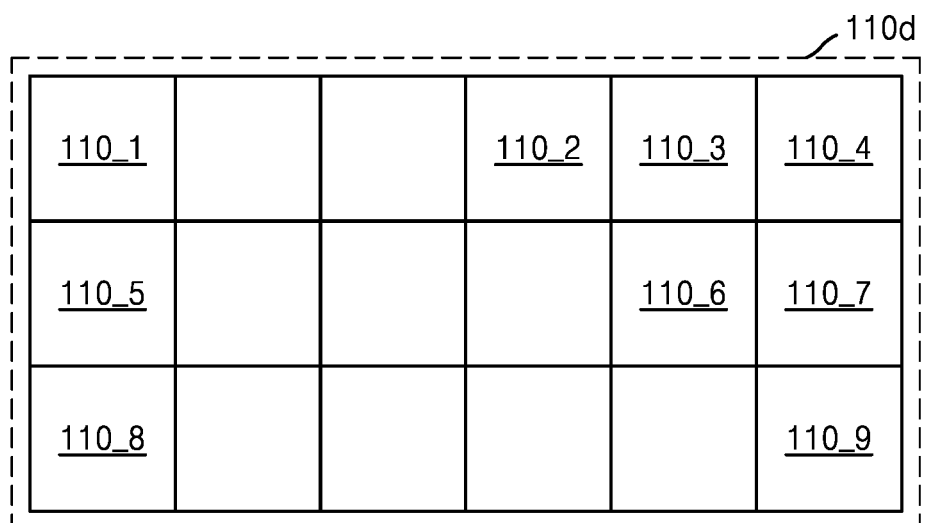

Referring to FIG. 3D, optical sensors 110d may include first to ninth optical sensors 110_1 to 110_9. According to an example embodiment, second to fourth optical sensors 110_2, 110_3, and 110_4 may be arranged a first distance apart from a first optical sensor 110_1, sixth and seventh optical sensors 110_6 and 110_7 may be arranged a second distance apart from a fifth optical sensor 110_5, and a ninth optical sensor 110_9 may be arranged a third distance apart from an eighth optical sensor 110_8. However, FIG. 3D is merely an example embodiment and is not limited thereto. For example, more optical sensors or fewer optical sensors may be arranged in various distances and aligned in various manners.

Figure 4:
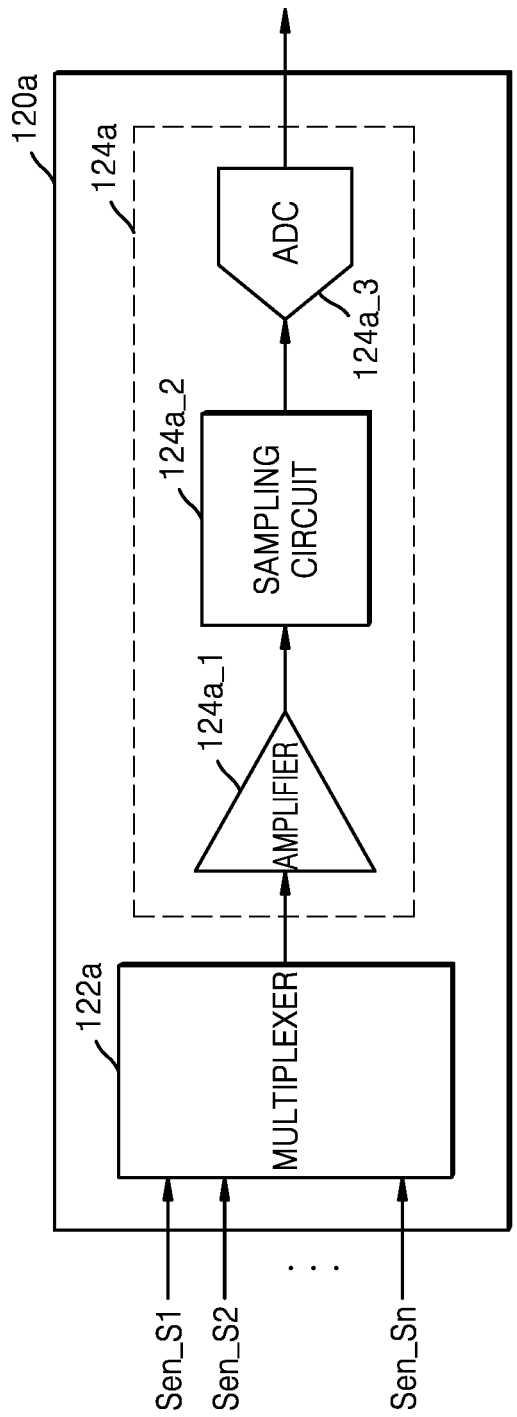
FIG. 4 is a block diagram showing an example implementation of a read-out signal generating circuit of FIG. 1.

FIG. 4 is a block diagram showing an example implementation of the read-out signal generating circuit 120 of FIG. 1.

Referring to FIG. 4, a read-out signal generating circuit 120a may include a multiplexer 122a and a read-out circuit 124a. The read-out circuit 124a may include an amplifier 124a_1, a sampling circuit 124a_2, and an analog-to-digital converter 124a_3. The multiplexer 122a may receive sensing signals Sen_S1 to Sen_Sn respectively from the optical sensors 110 (FIG. 1) and provide the sensing signals Sen_S1 to Sen_Sn to the read-out circuit 124a. According to an example embodiment, the multiplexer 122a may receive the sensing signals Sen_S1 to Sen_Sn and sequentially and/or selectively provide the sensing signals Sen_S1 to Sen_Sn to the read-out circuit 124a.

The amplifier 124a_1 may amplify the sensing signals Sen_S1 to Sen_Sn that are received and provide them to the sampling circuit 124a_2, and the sampling circuit 124a_2 may sample the sensing signals Sen_S1 to Sen_Sn and generate sample signals. The sampling circuit 124a_2 may provide the sample signals to the analog-to-digital converter 124a_3, and the analog-to-digital converter 124a_3 may convert the sample signals, which are analog signals, into digital signals. Moreover, the digital signal may be referred to as read-out signals. The analog-to-digital converter 124a_3 may provide digital signals to the signal processing circuit 130 (FIG. 1).

Figure 5:
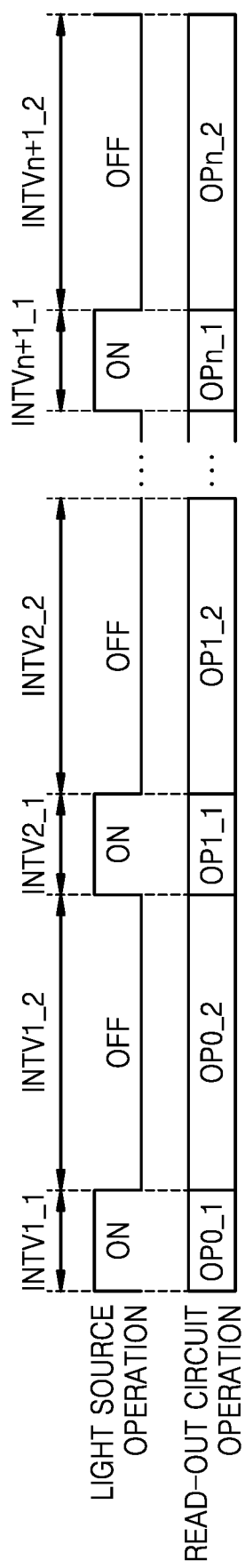
FIG. 5 is a timing diagram for describing the operation of the PPG sensing module of FIG. 1.

FIG. 5 is a timing diagram for describing the operation of the PPG sensing module 1 of FIG. 1. In FIG. 5, it is assumed that the implementation example shown in FIG. 4 is applied to the read-out signal generating circuit 120.

Referring to FIGS. 1 and 5, in an interval 1_1 INTV1_1, the light source 10 may be turned on and output light, the optical sensors 110 may receive light reflected from a blood vessel and generate sensing signals, and the read-out signal generating circuit 120 may perform an operation 1_1 OP0_1. The operation 1_1 OP0_1 may include a series of operations for generating sample signals by sequentially amplifying and sampling the sensing signals generated by the optical sensors 110. In an interval 1_2 INTV1_2, the light source 10 may be turned off, and the read-out signal generating circuit 120 may perform an operation 1_2 OP0_2 for converting the sample signals generated in the interval 1_1 INTV1_1 into digital signals. The signal processing circuit 130 may generate a PPG signal by using the digital signals generated in the interval 1_2 INTV1_2.

In an interval 2_1 INTV2_1, the light source 10 may be turned on again and output light, the optical sensors 110 may receive reflected light reflected from the blood vessel and generate sensing signals, and the read-out signal generating circuit 120 may perform an operation 2_1 OP1_1. The operation 2_1 OP1_1 may include a series of operations for generating a sample signal by amplifying and sampling a sensing signal generated by at least one first optical sensor from among the optical sensors 110. In an interval 2_2 INTV2_2, the light source 10 may be turned off again, and the read-out signal generating circuit 120 may perform an operation 2_2 OP1_2 for converting the sample signal generated in the interval 2_1 INTV2_1 into a digital signal. In an interval n+1_1 INTVn+1_1, the light source 10 may be turned on again and output light, the optical sensors 110 may receive reflected light reflected from the blood vessel and generate sensing signals, and the read-out signal generating circuit 120 may perform an operation n+1_1 OPn_1. The operation n+1_1 OPn_1 may include a series of operations for generating a sample signal by amplifying and sampling a sensing signal generated by at least one n-th optical sensor from among the optical sensors 110. In an interval n+1_2 INTVn+1_2, the light source 10 may be turned off again, and the read-out signal generating circuit 120 may perform an operation n+1_2 OPn_2 for converting the sample signal generated in the interval n+1_1 INTVn_1 into a digital signal. The signal processing circuit 130 may measure movement components of a user by using digital signals generated in a plurality of intervals INTV2_1, INTV2_2 to INTVn+1_1, and INTVn+1_2. The signal processing circuit 130 may remove movement components measured by using digital signals generated in the other intervals INTV2_1 to INTVn+1_2 from a PPG signal generated by using digital signals generated in some intervals INTV1_1 and INTV1_2, thereby generating an accurate PPG signal. The other intervals INTV2_1 to INTVn+1_2 may be referred to as sub-intervals for measuring movement components. The PPG sensing module 1 may be used to measure movement components by converting sensing signals generated by different optical sensors in the respective sub-intervals into digital signals. Moreover, the read-out signal generating circuit 120 may perform periodic ON/OFF control for the light source 10.

According to an example embodiment, the PPG sensing module 1 may measure movement components based on the amount of change between digital signals generated in intervals before the interval 1_1 INTV1_1 and digital signals generated in later intervals INTV1_1 to INTVn+1_2.

Figure 6:
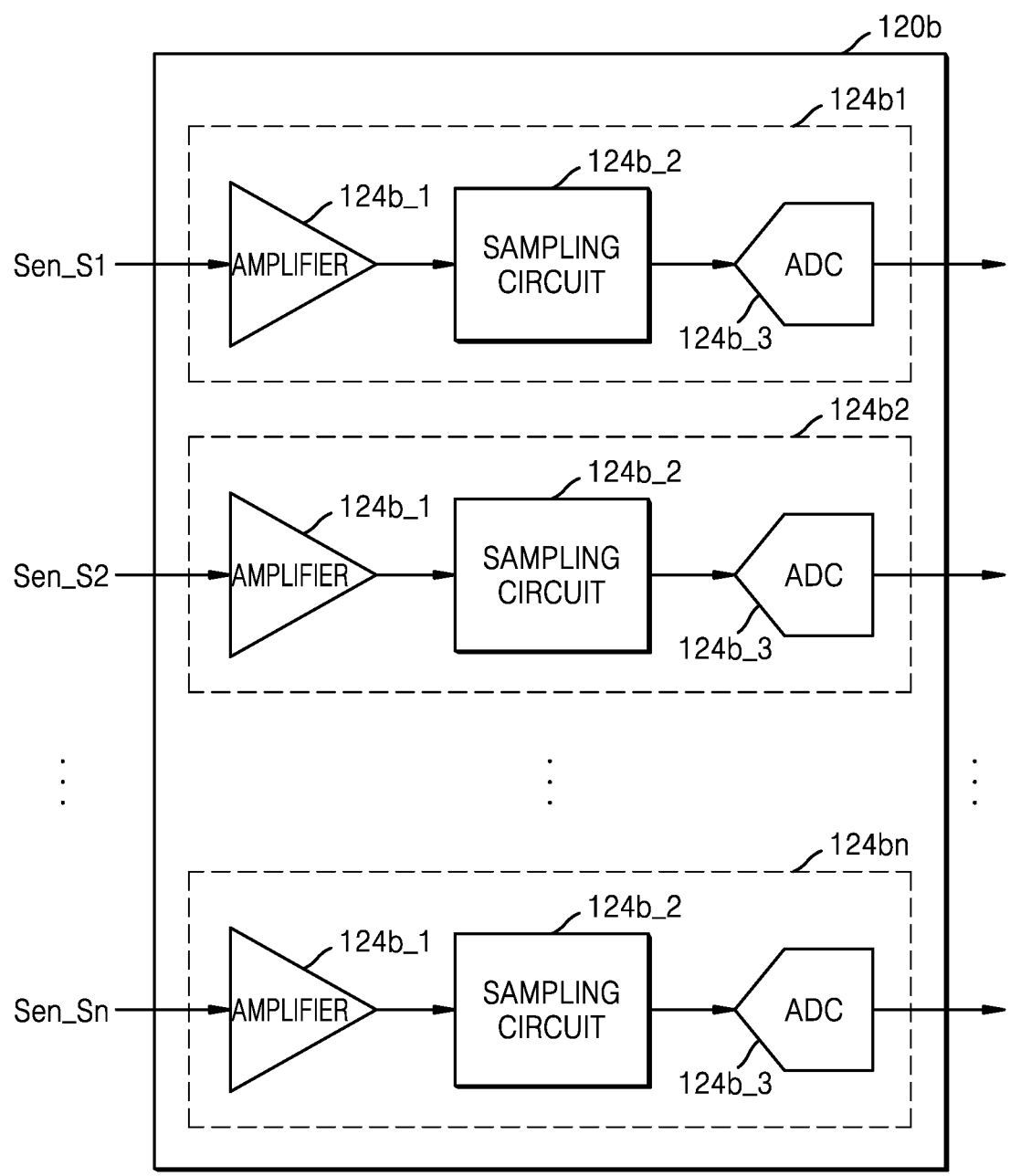
FIG. 6 is a block diagram showing an example implementation of a read-out signal generating circuit of FIG. 1.

FIG. 6 is a block diagram showing an example implementation of the read-out signal generating circuit 120 of FIG. 1.

Referring to FIG. 6, a read-out signal generating circuit 120b may include first to n-th read-out circuits 124b1 to 124bn. The first read-out circuit 124b1 may include an amplifier 124b_1, a sampling circuit 124b_2, and an analog-to-digital converter 124b_3. The second to n-th read-out circuits 124b2 to 124bn may also be implemented with the same configuration as that of the first read-out circuit 124b1.

The first to n-th read-out circuits 124b1 to 124bn may individually receive first to n-th sensing signals Sen_S1 to Sen_Sn, respectively. In other words, the number of optical sensors of a PPG sensing module may be n, and the first to n-th read-out circuits 124b1 to 124bn may be respectively connected to the optical sensors and receive sensing signals from the connected optical sensors. For example, the first read-out circuit 124b1 receives a first sensing signal Sen_S1 from a first optical sensor and generates a digital signal by amplifying, sampling, and analog-to-digital converting the first sensing signal Sen_S1. The first to n-th read-out circuits 124b1 to 124bn may generate digital signals from the first to n-th sensing signals Sen_S1 to Sen_Sn and simultaneously output them to the signal processing circuit 130 as shown in FIG. 1. In an example embodiment, the signal processing circuit 130 may generate a PPG signal by summing the first to n-th sensing signals Sen_S1 to Sen_Sn, and may measure movement components from the first to n-th sensing signal Sen_S1 to Sen_Sn, and remove the movement components from the generated PPG signal.

Figure 7:
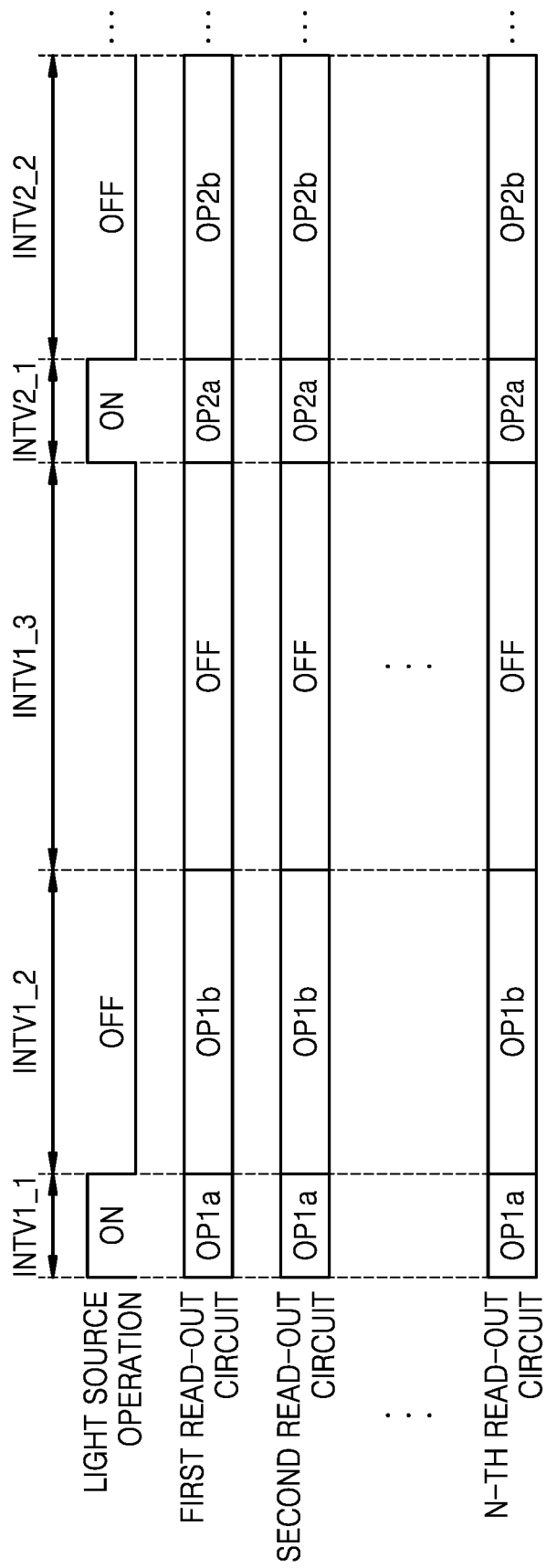
FIG. 7 is a timing diagram for describing the operation of the PPG sensing module of FIG. 1.

FIG. 7 is a timing diagram for describing the operation of the PPG sensing module 1 of FIG. 1. In FIG. 7, it is assumed that the implementation example shown in FIG. 6 is applied to the read-out signal generating circuit 120.

Referring to FIGS. 1 and 7, in an interval 1_1 INTV1_1, the light source 10 may be turned on and output light, the optical sensors 110 may receive light reflected from a blood vessel and generate sensing signals, and first to n-th read-out circuits of the read-out signal generating circuit 120 may each perform a first operation OP1a. The first operation OP1a may include a series of operations for generating a sample signal by amplifying and sampling a sensing signal generated by an optical sensor to which each read-out circuit is connected. In an interval 1_2 INTV1_2, the light source 10 is turned off and the first to n-th read-out circuits may each perform a second operation OP1b. The second operation OP1b may include an operation for converting a sample signal generated in the interval 1_1 INTV1_1 into a digital signal. In an interval 1_3 INTV1_3, the first to n-th read-out circuits may be turned off or deactivated, and the signal processing circuit 130 may generate a PPG signal and movement components by using digital signals generated by the first to n-th read-out circuits and remove the movement components from the PPG signal.

Thereafter, the PPG sensing module 1 may perform operations OP2a and OP2b in the interval 2_1 INTV2_1, the interval 2_2 INTV2_2, and an interval 2_3 in the same manner as in intervals 1_1 to 1_3 INTV1_1 to INTV1_3, thereby outputting a PPG signal from which movement components are removed.

Figure 8:
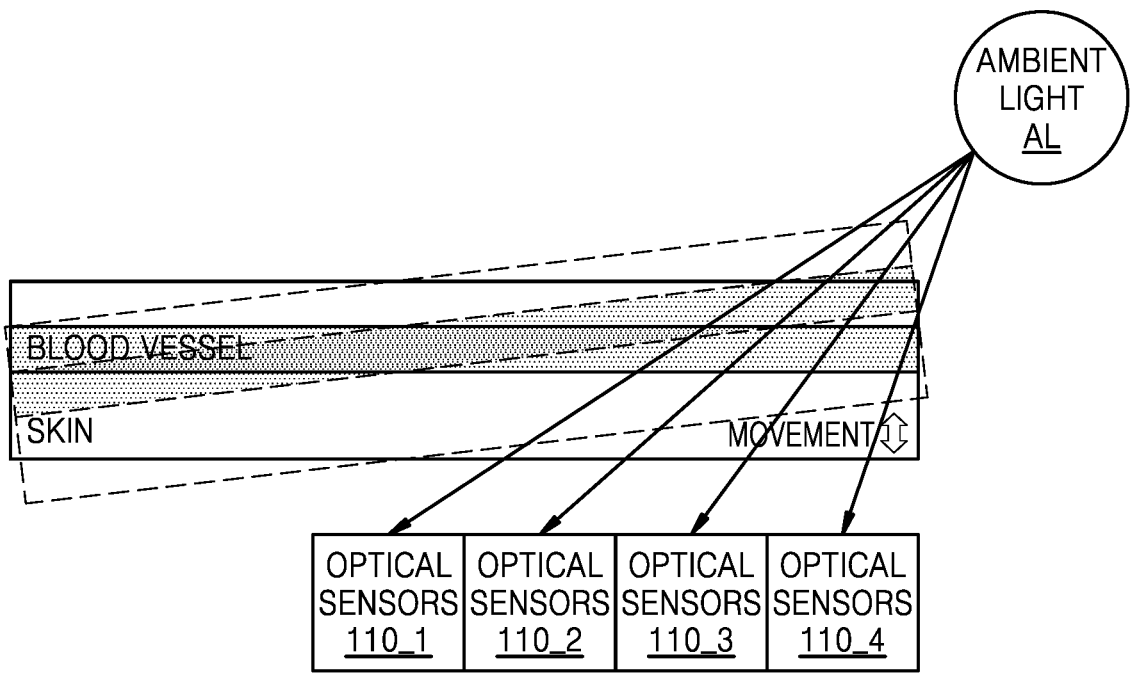
FIG. 8 is a diagram for describing an embodiment for using ambient light to measure the movement components in a PPG signal.

FIG. 8 is a diagram for describing an embodiment for using ambient light AL to measure the movement components in a PPG signal. Hereinafter, descriptions identical to those already given above with reference to FIG. 2 will be omitted.

A PPG sensing module according to an example embodiment of the inventive concept may use the ambient light AL to measure movement components of a user in a PPG signal. Referring to FIG. 8, the position of a blood vessel through which the ambient light AL passes or scatters may be changed according to a movement of a user, and thus, light received by first to fourth optical sensors 110_1 to 110_4 may be distorted. Therefore, the PPG sensing module may measure movement components from a PPG signal by using sensing signals that are generated by the optical sensors 110_1 to 110_4 by receiving the ambient light AL According to an example embodiment, the PPG sensing module may use the light source 10 (as shown in FIG. 1) to generate a PPG signal and may use the ambient light AL to measure movement components. Therefore, the PPG sensing module may minimize power consumed by the light source 10.

Figure 9:
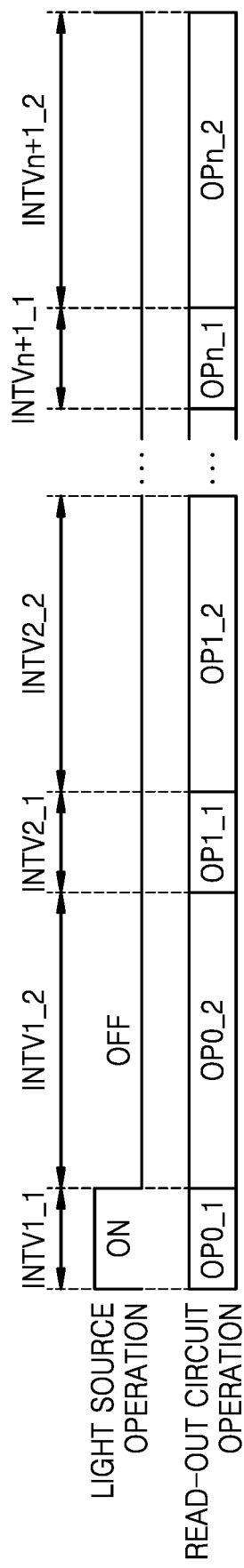
FIG. 9 is a timing diagram for describing the operation of the PPG sensing module of FIG. 1.

FIG. 9 is a timing diagram for describing the operation of the PPG sensing module 1 of FIG. 1. In FIG. 9, it is assumed that the implementation example shown in FIG. 4 is applied to the read-out signal generating circuit 120 and movement components are measured by using the ambient light AL as shown in FIG. 8.

Referring to FIGS. 1 and 9, in an interval 1_1 INTV1_1, the light source 10 may be turned on and output light, the optical sensors 110 may receive light reflected from a blood vessel and generate sensing signals, and the read-out signal generating circuit 120 may perform an operation 1_1 OP0_1. The operation 1_1 OP0_1 may include a series of operations for generating sample signals by sequentially amplifying and sampling the sensing signals generated by the optical sensors 110. In an interval 1_2 INTV1_2, the light source 10 may be turned off, and the read-out signal generating circuit 120 may perform an operation 1_2 OP0_2 for converting the sample signals generated in the interval 1_1 INTV1_1 into digital signals. The signal processing circuit 130 may generate a PPG signal by using the digital signals generated in the interval 1_2 INTV1_2.

In the interval 2_1 INTV2_1, the optical sensors 110 may receive the ambient light AL as shown in FIG. 8 that passed through or scattered by a blood vessel and generate ambient sensing signals, and the read-out signal generating circuit 120 may perform the operation 2_1 OP1_1. The operation 2_1 OP1_1 may include a series of operations for generating a sample signal by amplifying and sampling an ambient sensing signal generated by at least one first optical sensor from among the optical sensors 110. In the interval 2_2 INTV2_2, the read-out signal generating circuit 120 may perform the operation 2_2 OP1_2 for converting the sample signal generated in the interval 2_1 INTV2_1 into a digital signal. In the interval n+1_1 INTVn+1_1, the optical sensors 110 may receive the ambient light AL that passed through or scattered by a blood vessel and generate ambient sensing signals, and the read-out signal generating circuit 120 may perform the operation n+1_1 OPn_1. The operation n+1_1 OPn_1 may include a series of operations for generating a sample signal by amplifying and sampling an ambient sensing signal generated by at least one n-th optical sensor from among the optical sensors 110. In the interval n+1_2 INTVn+1_2, the read-out signal generating circuit 120 may perform the operation n+1_2 OPn_2 for converting the sample signal generated in the interval n+1_1 INTVn+1_1 into a digital signal. The signal processing circuit 130 may measure movement components of a user by using digital signals generated in a plurality of intervals INTV2_1 and INTVn+1_2. The signal processing circuit 130 may remove movement components measured by using digital signals generated in the other intervals INTV2_1 to INTVn+1_2 from a PPG signal generated by using digital signals generated in some intervals INTV1_1 and INTV1_2, thereby generating an accurate PPG signal.

Figure 10:
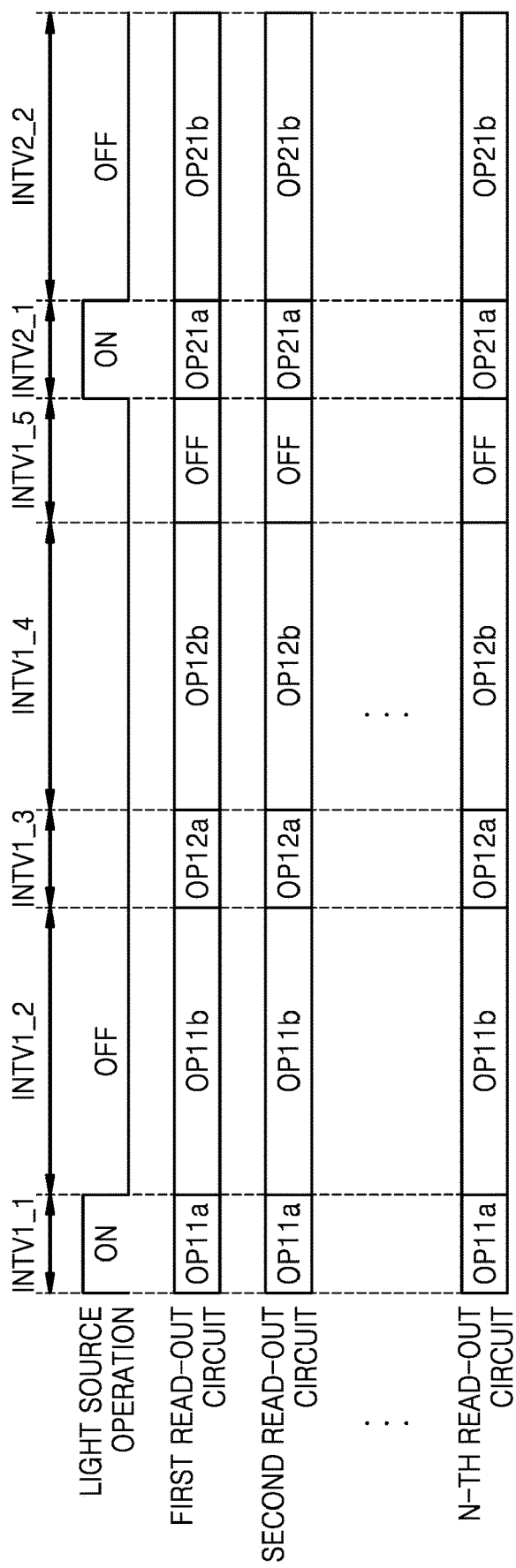
FIG. 10 is a timing diagram for describing the operation of the PPG sensing module of FIG. 1.

FIG. 10 is a timing diagram for describing the operation of the PPG sensing module 1 of FIG. 1. In FIG. 10, it is assumed that the implementation example shown in FIG. 6 is applied to the read-out signal generating circuit 120 and movement components are measured by using the ambient light AL as shown in FIG. 8.

Referring to FIGS. 1 and 10, in the interval 1_1 INTV1_1, the light source 10 may be turned on and output light, the optical sensors 110 may receive light reflected from a blood vessel and generate sensing signals, and first to n-th read-out circuits of the read-out signal generating circuit 120 may each perform an operation 1_1 OP11 a. The operation 1_1 OP11 a may include a series of operations for generating a sample signal by amplifying and sampling a sensing signal generated by an optical sensor to which each read-out circuit is connected. In an interval 1_2 INTV1_2, the light source 10 is turned off, and the first to n-th read-out circuits may each perform an operation 1_2 OP11b. The operation 1_2 OP11b may include an operation in which each read-out circuit converts a sample signal generated at the interval 1_1 INTV1_1 into a digital signal. The signal processing circuit 130 may generate a PPG signal by using the digital signals generated in the interval 1_2 INTV1_2.

In the interval 1_3 INTV1_3, the optical sensors 110 may receive the ambient light AL (FIG. 8) that passed through or scattered by a blood vessel and generate ambient sensing signals, and the first to n-th read-out circuits of the read-out signal generating circuit 120 may perform an operation 1_3 OP12a. The operation_3 OP12a may include a series of operations for generating a sample signal by amplifying and sampling an ambient sensing signal generated by an optical sensor to which each read-out circuit is connected. In an interval 1_4 INTV1_ 4, the first to n-th read-out circuits may each perform an operation 1_4 OP12b. The operation 1_4 OP12b may include an operation in which each read-out circuit converts a sample signal generated at the interval 1_3 INTV1_3 into a digital signal. The first to n-th read-out circuits may be turned off or deactivated in an interval 1_5 INTV1_5. The signal processing circuit 130 may measure movement components by using digital signals generated by the first to n-th read-out circuits by using the ambient light AL (FIG. 8). Also, the signal processing circuit 130 may remove the movement component measured by using the ambient light AL (FIG. 8) from a PPG signal generated through the light source 10.

Thereafter, the PPG sensing module 1 may perform operations OP21a, OP21b, and so on in the interval 2_1 INTV2_1, the interval 2_2 INTV2_2, and intervals 2_3 to 2_5 in the same manner as in intervals 1_1 to 1_5 INTV1_1 to INTV1_5, thereby outputting a PPG signal from which movement components are removed.

Figure 11:
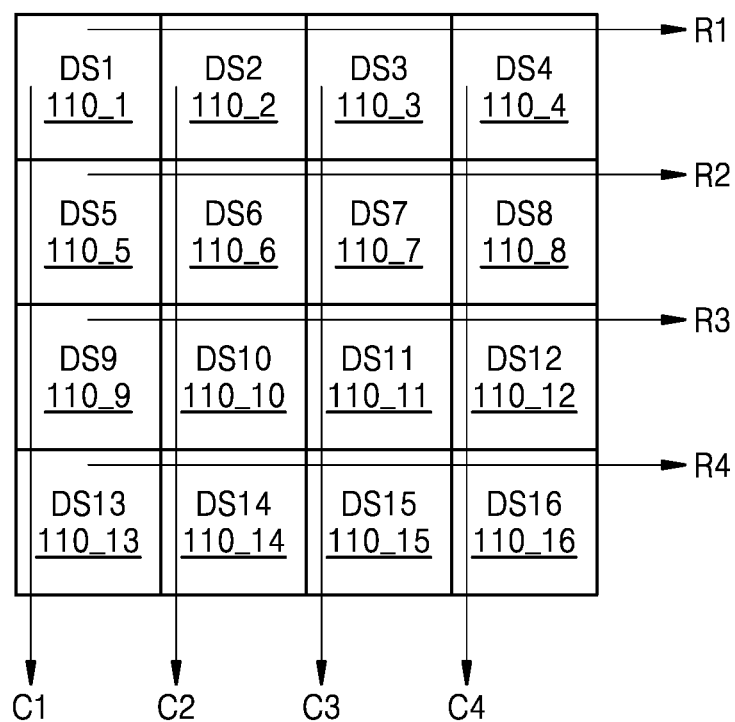
FIG. 11 is a diagram for describing a method of measuring movement components according to an example embodiment of the inventive concept.

FIG. 11 is a diagram for describing a method of measuring movement components according to an example embodiment of the inventive concept. Hereinafter, description will be given based on an example in which the optical sensors 110_1 to 110_16 are arranged 4×4. However, it will be understood that it is merely an example embodiment, and the inventive concept is not limited thereto.

Referring to FIGS. 1 and 11, the movement measuring circuit 132 may receive first to sixteenth digital signals DS1 to DS16 generated by the read-out signal generating circuit 120. The first to sixteenth digital signals DS1 to DS16 may correspond to first to sixteenth optical sensors 110_1 to 110_16, and the first to sixteenth digital signals DS1 to DS16 may include position information regarding corresponding optical sensors, respectively.

According to an example embodiment, the movement measuring circuit 132 may classify the first to sixteenth digital signals DS1 to DS16 based on first to fourth rows R1 to R4 or classify the first to sixteenth digital signals DS1 to DS16 based on first to fourth columns C1 to C4. According to an example embodiment, the movement measuring circuit 132 may measure movement components by comparing sum values of digital signals of each row to one another considering a user's movement pattern. For example, the movement measuring circuit 132 may sum first to fourth digital signals DS1 to DS4 corresponding to a first row R1, sum fifth to eighth digital signals DS5 to DS8 corresponding to a second row R2, and compare the sum value corresponding to the first row R1 with the sum value corresponding to the second row R2. The movement measuring circuit 132 may measure movement components corresponding to a movement pattern in a certain column-wise direction based on a result of the comparison.

However, the classification and measurement of movement components based on a row-wise or a column-wise direction is merely an example embodiment. Digital signals may be classified not only based on rows R1 to R4 and columns C1 to C4, but also based on diagonal directions or in other patterns considering a movement pattern of a user, and movement components may be measured by comparing sums of classified digital signals to each other.

Furthermore, in an example embodiment, the movement measuring circuit 132 may normalize first, fourth, thirteenth, and sixteenth digital signals DS1, DS4, DS13, and DS16 located at the corners, and movement components may be measured by calculating changes in relative values of the other digital signals D2, DS3, DS5 to DS12, DS14, and DS15 based on the normalized first, fourth, thirteenth, and sixteenth digital signals DS1, DS4, DS13, and DS16.

Furthermore, in an example embodiment, the movement measuring circuit 132 may classify left digital signals into digital signals DS1, DS2, DS5, DS6, DS9, DS10, DS13, and DS14 and right digital signals DS3, DS4, DS7, DS8, DS11, DS12, DS15, and DS16 and measure movement components by comparing sums thereof with each other. Furthermore, the movement measuring circuit 132 may classify digital signals into upper digital signals DS1 to DS8 and lower digital signals DS9 to DS16 and measure movement components by comparing sums thereof with each other.

Although the descriptions of FIG. 11 have been given based on embodiments of the optical sensors 110_1 to 110_16 arranged 4×4, it is merely an example embodiment, and the inventive concept for classifying digital signals considering movement patterns of a user and measuring movement components by comparing sums of digital signals classified according to respective movement patterns with each other may be applied to various other optical sensor structures such as structures with various shapes and/or sizes.

Figure 12A:
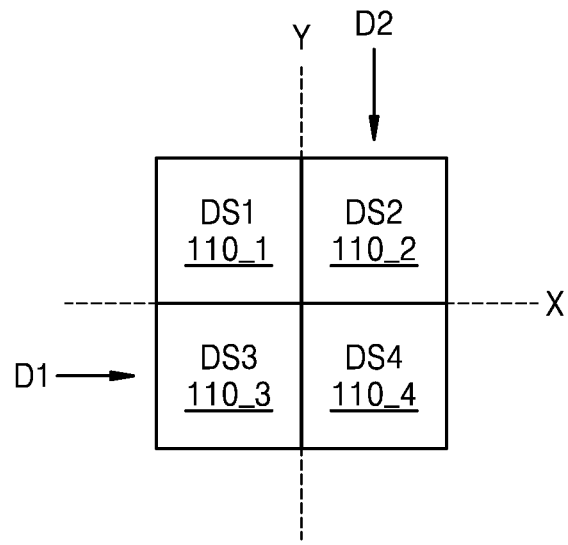
FIGS. 12A to 12C are diagrams for describing a method of measuring movement components according to an example embodiment of the inventive concept.
Figure 12B:
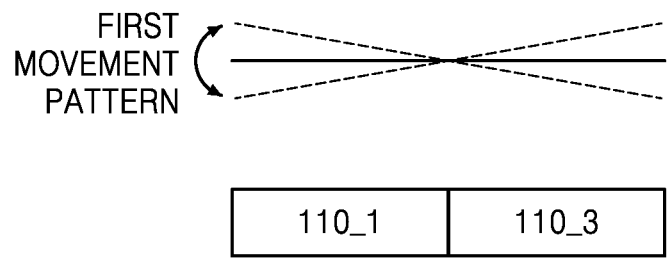
Figure 12C:
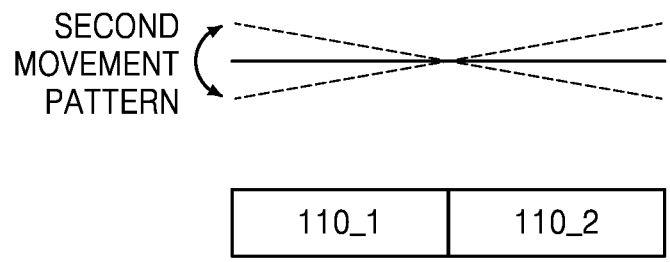

FIGS. 12A to 12C are diagrams for describing a method of measuring movement components according to an example embodiment of the inventive concept. Hereinafter, description will be given based on an example in which the first to fourth optical sensors 110_1 to 110_4 are arranged 2×2. However, it will be understood that it is merely an example embodiment, and the inventive concept is not limited thereto.

Referring to FIGS. 1 and 12A, the movement measuring circuit 132 may receive first to fourth digital signals DS1 to DS4 generated by the read-out signal generating circuit 120. The first to fourth digital signals DS1 to DS4 may correspond to first to fourth optical sensors 110_1 to 110_4, and the first to fourth digital signals DS1 to DS4 may include position information corresponding to each of the optical sensors, respectively.

In an example embodiment, the movement measuring circuit 132 may classify first and second digital signals DS1 and DS2 as a first signal group and third and fourth digital signals DS3 and DS4 as a second signal group based on an X axis. A movement component according to a first movement pattern may be measured by comparing the sum of first and second digital signals DS1 and DS2 of the first signal group with the sum of third and fourth digital signals DS3 and DS4 of the second signal group.

Further referring to FIGS. 12A and 12B, when viewed in a first direction D1 parallel to the X-axis, the movement measuring circuit 132 may measure a movement component according to the first movement pattern of a user corresponding to an Y-axis by comparing the first and second digital signals DS1 and DS2 of the first signal group with the third and fourth digital signals DS3 and DS4 of the second signal group. In detail, the movement measuring circuit 132 may measure the movement component according to the first movement pattern by using an equation as shown below.

$$\text{movement component} = \frac{\frac{DS1 + DS2}{2} - \frac{DS3 + DS4}{2}}{\frac{DS1 + DS2 + DS3 + DS4}{4}}$$

According to an example embodiment, the movement measuring circuit 132 may measure a movement component by subtracting an average of the sum of the third and fourth digital signals DS3 and DS4 of the second signal group from an average of the sum of the first and second digital signals DS1 and DS2 of the first signal group and dividing a subtraction result by an average of the first to fourth digital signals DS1 to DS4. The movement measuring circuit 132 may reduce errors of movement measurement through such an operation.

Referring back to FIG. 12A, the movement measuring circuit 132 may determine whether a movement component measured considering the first movement pattern exceeds a critical value, and, when the critical value is not exceeded, the movement measuring circuit 132 may measure a movement component by considering a second movement pattern. In an example embodiment, the movement measuring circuit 132 may classify first and third digital signals DS1 and DS3 as a first signal group and second and fourth digital signals DS2 and DS4 as a second signal group based on an X axis. A movement component according to the second movement pattern may be measured by comparing the sum of the first and third digital signals DS1 and DS3 of the first signal group with the sum of the second and fourth digital signals DS2 and DS4 of the second signal group. Moreover, when the movement component measured considering the first movement pattern exceeds the critical value, the movement measuring circuit 132 may provide the movement component to the PPG signal generating circuit 134, such that the movement component may be removed from a PPG signal.

Further referring to FIGS. 12A and 12C, when viewed in a second direction D2 parallel to the Y-axis, the movement measuring circuit 132 may measure a movement component according to the second movement pattern of a user corresponding to the X-axis by comparing the first and third digital signals DS1 and DS3 of the first signal group with the second and fourth digital signals DS2 and DS4 of the second signal group. In detail, the movement measuring circuit 132 may measure the movement component according to the second movement pattern by using an equation as shown below.

$$\text{movement component} = \frac{\frac{DS1 + DS3}{2} - \frac{DS2 + DS4}{2}}{\frac{DS1 + DS2 + DS3 + DS4}{4}}$$

In other words, the movement measuring circuit 132 may measure a movement component by subtracting an average of the sum of the second and fourth digital signals DS2 and DS4 of the second signal group from an average of the sum of the first and third digital signals DS1 and DS3 of the first signal group and dividing a subtraction result by an average of the first to fourth digital signals DS1 to DS4.

However, the embodiments shown in FIGS. 12A to 12C are merely examples, and the inventive concept is not limited thereto. The movement measuring circuit 132 may classify digital signals in various ways considering movement patterns and measure movement components by comparing them in various ways.

Figure 13:
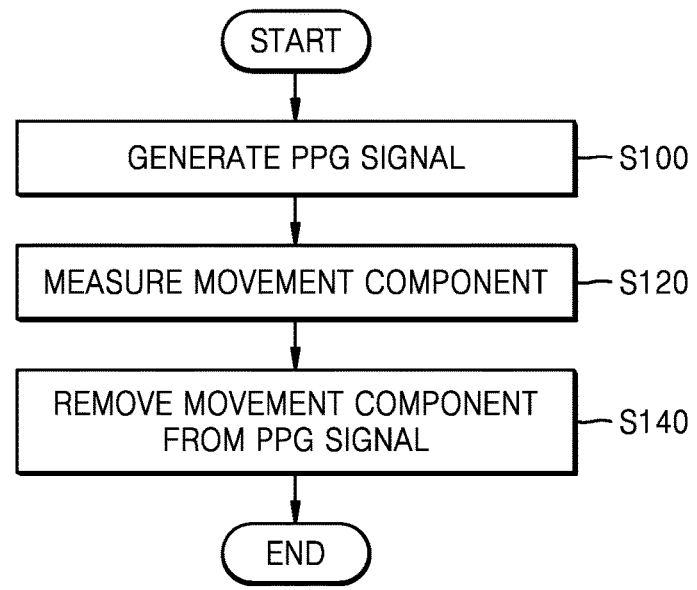
FIG. 13 is a flowchart of a method of operating a PPG sensing module according to an example embodiment of the inventive concept.
Figure 14:
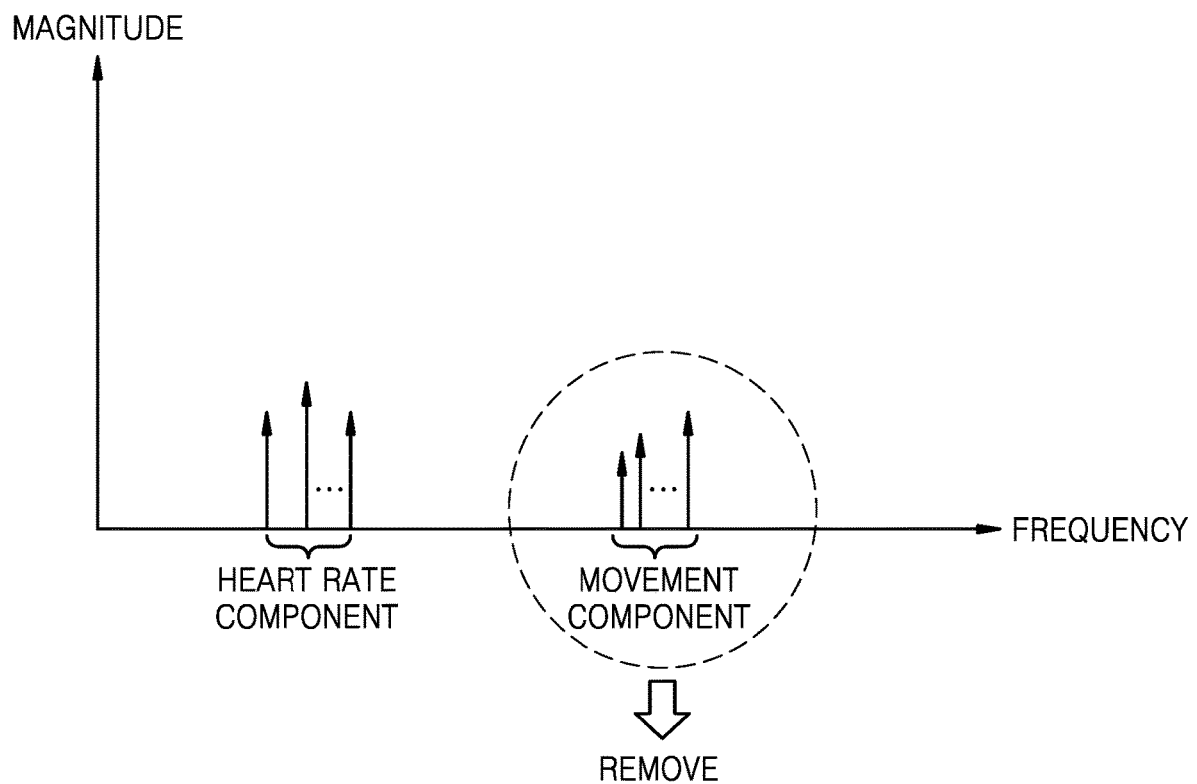
FIG. 14 is a graph for describing operation S140 in detail.

FIG. 13 is a flowchart of a method of operating a PPG sensing module according to an example embodiment of the inventive concept, and FIG. 14 is a graph for describing operation S140 in detail.

Referring to FIG. 13, in operation S100, a PPG sensing module may generate sensing signals through a plurality of optical sensors, which receive light irradiated from a light source and reflected by a blood vessel of a user, and generate a PPG signal by using the sensing signals. In a situation when there is a movement from a user while the PPG sensing module is generating a PPG signal of the user, it is difficult to generate an accurate PPG signal. Therefore, in operation S120, the PPG sensing module may classify digital signals generated from sensing signals of the optical sensors considering movement patterns of the user and measure movement components by comparing the classified digital signals to each other. The PPG sensing module may repeat movement component measuring operations respectively corresponding to various movement patterns of the user for a plurality of number of times. In operation S140, the PPG sensing module may remove a movement component from the PPG signal and provide an accurately measured PPG signal to the user.

Further referring to FIG. 14, a PPG signal generated by the PPG sensing module may include a heart rate component and a movement component. The heart rate component and the movement component may be in different frequency domains. That is, the PPG signal may include a heart rate component in a first frequency domain and a movement component in a second frequency domain. The PPG sensing module may recognize the frequency domain of the movement component by measuring the movement component and remove the movement component by applying a frequency filter to the PPG signal.

Figure 15:
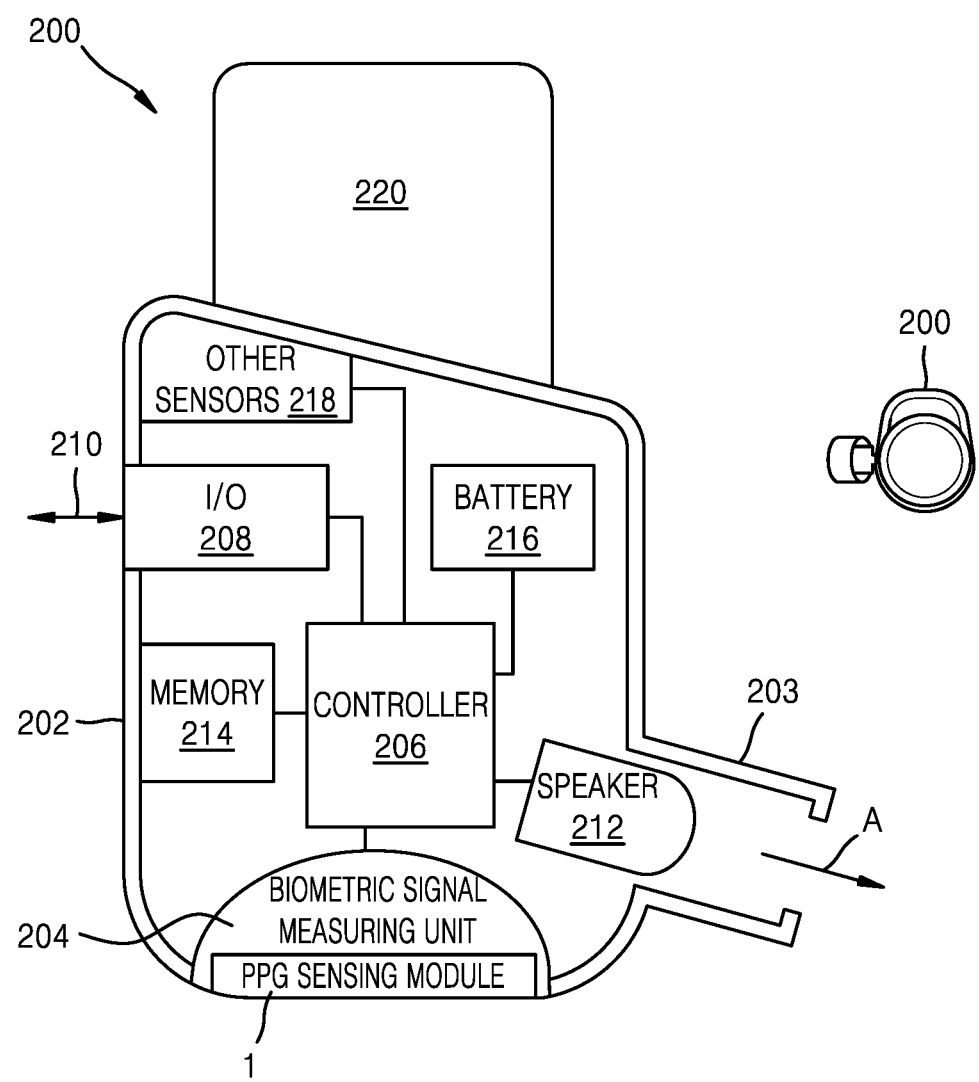
FIG. 15 is a diagram showing an earphone to which example embodiments of the inventive concept are applied.

FIG. 15 is a diagram showing an earphone 200 to which example embodiments of the inventive concept are applied.

Referring to FIG. 15, the earphone 200 may include a housing 202, and the housing 202 may have a size and/or a shape for facilitating insertion of the housing 202 into an ear of a user. The housing 202 may define an internal space in which a plurality of electrical components may be distributed. For example, a biometric signal measuring unit 204 may be located inside the housing 202 or supported by the housing 202. The biometric signal measuring unit 204 may be arranged in an opening of the housing 202. Accordingly, the biometric signal measuring unit 204 may include an outer facing sensing surface capable of interacting with and measuring external stimuli. The housing 202 may include a protrusion 203 that provides a channel through which an audio signal may be transmitted in and out of an ear canal of a user of the earphone 200, as indicated by the arrow (A).

The biometric signal measuring unit 204 may include the PPG sensing module 1 according to example embodiments of the inventive concept, wherein a plurality of optical sensors of the PPG sensing module 1 may be in contact with an ear of a user or variously arranged at positions closest to the ear. For example, the plurality of optical sensors of the PPG sensing module 1 may be in direct contact with the ear of the user. The PPG sensing module 1 may measure movement components considering movement patterns of a user by using sensing signals received through the optical sensors, as in the above-described embodiments.

The biometric signal measuring unit 204 may be in electrical communication with the controller 206, which may control various aspects of the earphone 200. For example, the controller 206 may collect biometric data (e.g., PPG signal data) recorded by the biometric signal measuring unit 204 and transmit the biometric data to an input/output (I/O) interface 208. The input/output interface 208 may be configured to exchange biometric data with other devices (e.g., a portable media device) via a wireless link 210.

According to an example embodiment, when a movement component measured by the PPG sensing module 1 exceeds a certain critical value, the controller 206 may provide an audio signal, which informs that data or information related to a PPG signal may not be smoothly provided, to a user via a speaker 212.

The earphone 200 may further include a memory 214 for storing certain data for performing plurality of tasks, and the PPG sensing module 1 may measure a movement component by using the memory 214 and remove a movement component from a PPG signal. Also, the memory 214 may store biometric data including a PPG signal from which a movement component is removed according to the above-described embodiments.

The earphone 200 may further include a battery 216 to provide power for the operation of the earphone 200. In detail, the battery 216 may supply power to maintain the wireless link 210, supply power to the controller 206, supply power to drive the speaker 212, supply power to the biometric signal measuring unit 204, and supply power to other sensors 218. The other sensors 218 may include a microphone, an orientation sensor, a proximity sensor, or any other sensor suitable for improving the user experience of the earphone 200.

Figure 16:
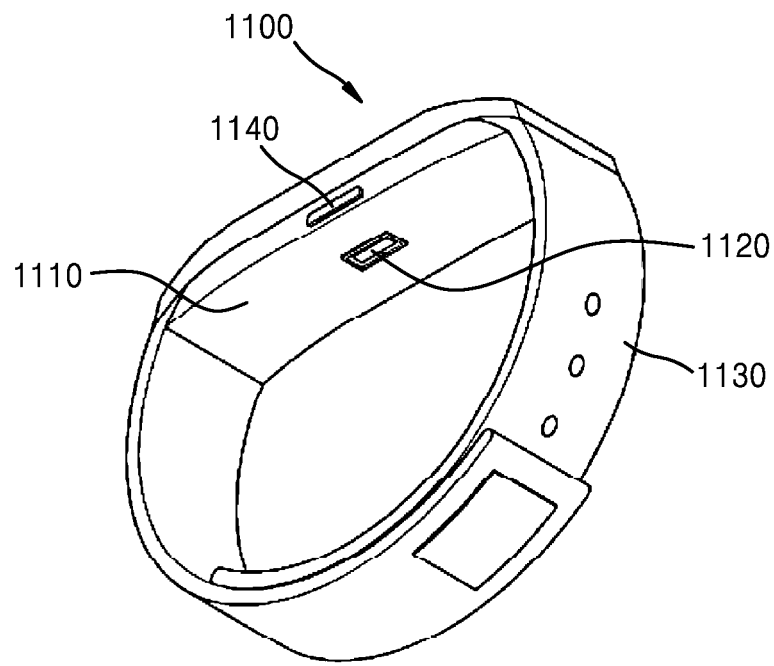
FIG. 16 is a diagram showing a wearable device to which example embodiments of the inventive concept are applied.

FIG. 16 is a diagram showing a wearable device 1100 to which example embodiments of the inventive concept are applied.

Referring to FIG. 16, the wearable device 1100 may include a main body 1110 and a strap 1130. The strap 1130 may be configured to be flexible, connected to both ends of the main body 1110, and bent in a form to be wrapped around a wrist of a user or to be separated from the wrist of the user. A battery that supplies power to the wearable device 1100 may be embedded in the main body 1100 or the strap 1130.

Also, the wearable device 1100 may include a biometric signal measuring unit 1120 for measuring a PPG signal from a user and a processor that monitors the PPG signal measured by the biometric signal measuring unit 1120 and generates biometric information about the user based on a result of the monitoring.

The biometric signal measuring unit 1120 may include a PPG sensing module 1 according to example embodiments of the inventive concept, wherein a plurality of optical sensors of the PPG sensing module 1 may be in contact with a wrist of a user or variously arranged at positions closest to the wrist. Here, the plurality of optical sensors of the PPG sensing module 1 may be in direct contact with the wrist of a user.

The wearable device 1100 may include a display mounted on a front surface of the main body 1110 and may visually output biometric signal measurement status monitoring results and/or biometric information measurement results. Also, when a movement component measured by the PPG sensing module exceeds a certain critical value, an image signal, which informs that data or information related to a PPG signal may not be smoothly provided, may be provided to a user via the display.

The wearable device 1100 may further include an operation unit 1140 that receives a control command from a user and transmits the control command to the processor. The operation unit 1140 may be mounted on a side surface of the main body 1110 and may include a function for inputting a command for turning the wearable device 1100 on/off. The wearable device 1100 may further include a communicator for exchanging various data with an external device and various other modules for performing additional functions provided by the wearable device 1100.

Figure 17:
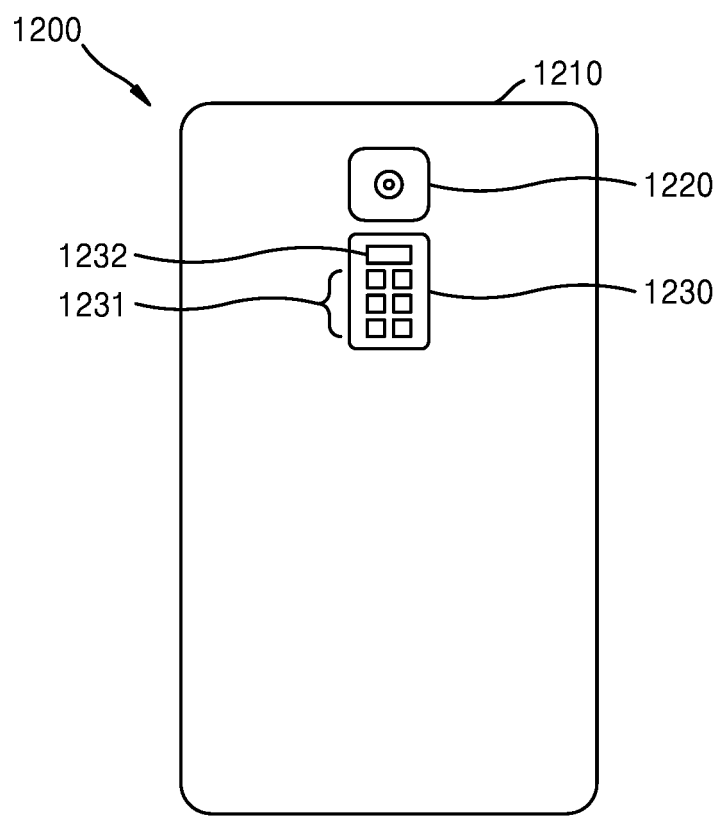
FIG. 17 is a diagram showing a smart device to which example embodiments of the inventive concept are applied.

FIG. 17 is a diagram showing a smart device 1200 to which example embodiments of the inventive concept are applied.

Referring to FIG. 17, the smart device 1200 may be implemented to have a biometric signal measuring unit 1230 exposed on the rear surface of a main body 1210. The biometric signal measuring unit 1230 may include one or more light sources 1231 and one or more optical sensors 1232. Also, the biometric signal measuring unit 1230 may further include a PPG sensing chip according to example embodiments of the inventive concept. The PPG sensing chip may include a PPG sensing module 1 according to example embodiments of the inventive concept. Also, a display may be provided on the front surface of the main body 1210. The display may visually the biometric signal measurement status monitoring results and biometric information measurement results. Also, when a movement component measured by the PPG sensing chip exceeds a certain critical value, an image signal, which informs that data or information related to a PPG signal may not be smoothly provided, may be provided to a user via the display.

Moreover, an image sensor 1220 may be provided on the main body 1210. When a user brings a target object (e.g., a finger) of the user close to the biometric signal measuring unit 1230 to measure a biometric signal of the user, the image sensor 1220 may capture an image of the finger and transmit the image of the finger to a processor. At this time, the processor may determine a relative position of the finger relative to an actual position of the biometric signal measuring unit 1230 from the image of the finger and provide information regarding the relative position of the finger to the user through the display, thereby facilitating precise biometric signal measurement. Various other modules for performing various functions of the above-described biometric information measuring device may be mounted on the smart device 1200, and detailed descriptions thereof will be omitted.

At least one of the components, elements, modules or units (collectively "components" in this paragraph) represented by a block in the drawing in FIG. 1 may be embodied as various numbers of hardware, software and/or firmware structures that execute respective functions described above, according to an exemplary embodiment. For example, at least one of these components may use a direct circuit structure, such as a memory, a processor, a logic circuit, a look-up table, etc. that may execute the respective functions through controls of one or more microprocessors or other control apparatuses. Also, at least one of these components may be specifically embodied by a module, a program, or a part of code, which contains one or more executable instructions for performing specified logic functions, and executed by one or more microprocessors or other control apparatuses. Further, at least one of these components may include or may be implemented by a processor such as a central processing unit (CPU) that performs the respective functions, a microprocessor, or the like. Two or more of these components may be combined into one single component which performs all operations or functions of the combined two or more components. Also, at least part of functions of at least one of these components may be performed by another of these components. Further, although a bus is not illustrated in the above block diagrams, communication between the components may be performed through the bus. Functional aspects of the above exemplary embodiments may be implemented in algorithms that execute on one or more processors. Furthermore, the components represented by a block or processing steps may employ any number of related art techniques for electronics configuration, signal processing and/or control, data processing and the like.

While the inventive concept has been particularly shown and described with reference to embodiments thereof, it will be understood that various changes in form and details may be made therein without departing from the spirit and scope of the following claims.

What is claimed is:

1. A photoplethysmogram (PPG) sensing module comprising:
   one or more light sources configured to emit light to a user;
   a plurality of optical sensors configured to receive reflected light from the user and generate a plurality of sensing signals, each of the plurality of sensing signals being generated by one of the plurality of optical sensors;
   a read-out signal generating circuit configured to receive the plurality of sensing signals from the plurality of optical sensors and generate a plurality of read-out signals by performing an analog-to-digital conversion on the plurality of sensing signals; and
   a signal processing circuit configured to:
      receive the plurality of read-out signals,
      classify the plurality of read-out signals according to one or more movement patterns of the user,
      measure a movement component of the user derived from the classified plurality of read-out signals, and
      generate a PPG signal in which the movement component is removed.

2. The PPG sensing module of claim 1, wherein the read-out signal generating circuit comprises:
   a multiplexer configured to be connected to outputs of the plurality of optical sensors; and
   a read-out circuit configured to be selectively connected to an output of one of the plurality of optical sensors through the multiplexer.

3. The PPG sensing module of claim 2, wherein the signal processing circuit is configured to:
   receive a plurality of first read-out signals corresponding to the plurality of optical sensors from the read-out circuit in a first interval,
   receive a plurality of second read-out signals corresponding to at least two of the plurality of optical sensors from the read-out circuit in a second interval subsequent to the first interval, and
   generate the PPG signal based on the plurality of first read-out signals, measure the movement component based on the plurality of second read-out signals, and remove the movement component from the PPG signal.

4. The PPG sensing module of claim 3, wherein the second interval comprises a plurality of sub-intervals, and
   the read-out signal generating circuit is configured to control the one or more light sources to be turned on/off for each of the plurality of sub-intervals and generate the plurality of second read-out signals by using sensing signals generated by different ones of the at least two of the plurality of optical sensors in the respective sub-intervals.

5. The PPG sensing module of claim 1, wherein the read-out signal generating circuit comprises a plurality of first read-out circuits configured to be connected to the plurality of optical sensors.

6. The PPG sensing module of claim 5, wherein the signal processing circuit is configured to:
simultaneously and individually receive the plurality of read-out signals corresponding to the plurality of optical sensors from the plurality of first read-out circuits, and
generate the PPG signal by summing the plurality of read-out signals and removing the movement component from the PPG signal.

7. The PPG sensing module of claim 1, wherein the signal processing circuit is configured to detect a first movement pattern, classify the plurality of read-out signals into a first signal group and a second signal group according to a first criterion, measure a first movement component corresponding to the first movement pattern by comparing the first signal group with the second signal group, and determine whether the first movement component exceeds a specified value.

8. The PPG sensing module of claim 7, wherein the signal processing circuit is configured to generate the PPG signal from which the first movement component is removed when the first movement component exceeds the specified value.

9. The PPG sensing module of claim 7, wherein when the first movement component is below the specified value, the signal processing circuit is configured to detect a second movement pattern, classify the plurality of read-out signals into a third signal group and a fourth signal group according to a second criterion and measure a second movement component corresponding to the second movement pattern by comparing the third signal group with the fourth signal group.

10. The PPG sensing module of claim 1, wherein the plurality of optical sensors are configured to receive ambient light other than the light from the one or more light sources and generate a plurality of ambient sensing signals,
the plurality of read-out signals comprise signals generated by performing an analog-to-digital conversion on the plurality of ambient sensing signals, and
the signal processing circuit is configured to measure the movement component by using signals generated from the plurality of ambient sensing signals.

11. The PPG sensing module of claim 10, wherein the plurality of optical sensors are configured to receive the ambient light in an interval where the one or more light sources are turned off and generate the plurality of ambient sensing signals.

12. The PPG sensing module of claim 1, wherein the plurality of optical sensors comprise first optical sensors configured to generate first sensing signals for generating the PPG signal and second optical sensors configured to generate second sensing signals for measuring the movement component.

13. A photoplethysmogram (PPG) sensing chip comprising:
a plurality of optical sensors configured to receive light from a user and generate a plurality of sensing signals, each of the plurality of sensing signals being generated by one of the plurality of optical sensors;
a read-out signal generating circuit configured to receive the plurality of sensing signals from the plurality of optical sensors and generate a plurality of read-out signals by performing an analog-to-digital conversion operation on the plurality of sensing signals; and
a signal processing circuit configured to:
receive the plurality of read-out signals,
generate a PPG signal by using the plurality of read-out signals,
measure a movement component of the user derived from position information about the plurality of optical sensors, and
remove the movement component from the PPG signal.

14. The PPG sensing chip of claim 13, wherein the plurality of sensing signals comprise a plurality of first sensing signals and a plurality of second sensing signals,
wherein the plurality of first sensing signals are generated based on light emitted from a certain light source to the user, reflected by the user, and received by the plurality of optical sensors,
wherein the plurality of second sensing signals are generated based on ambient light reflected by or transmitted through the user, and received by the plurality of optical sensors, and
wherein the signal processing circuit is configured to measure the movement component by using read-out signals corresponding to the plurality of second sensing signals from among the plurality of read-out signals.

15. The PPG sensing chip of claim 13, wherein the signal processing circuit is configured to classify the plurality of read-out signals into at least two signal groups by using position information about the plurality of optical sensors according to a criterion that matches a certain movement pattern of the user and measure the movement component by comparing the at least two signal groups with each other.

16. The PPG sensing chip of claim 13, wherein the signal processing circuit is configured to measure the movement component based on an amount of changes between previously generated read-out signals and the plurality of read-out signals, and
wherein the previously generated read-out signals are generated in a first interval before a second interval in which the plurality of read-out signals are generated.

17. The PPG sensing chip of claim 13, wherein the read-out signal generating circuit comprises a read-out circuit comprising an amplifier, a sample circuit, and an analog-to-digital converter to generate the read-out signal, and
wherein the read-out circuit is configured to sequentially generate and output read-out signals for generating the PPG signal to the signal processing circuit in a first interval and sequentially generate and output read-out signals for measuring the movement component to the signal processing circuit in a second interval subsequent to the first interval.

18. An apparatus comprising:
a memory storing one or more instructions; and
a processor configured to execute the one or more instructions to:
receive a plurality of read-out signals generated based on reflected light from a user that is detected by a plurality of optical sensors,
classify the plurality of read-out signals according to one or more movement patterns of the user,
measure a movement component of the user derived from the classified plurality of read-out signals, and
generate a photoplethysmogram (PPG) signal in which the movement component is removed.

19. The apparatus of claim 18, wherein the processor is further configured to classify the plurality of read-out signals according to one or more movement patterns of the user based on position information about one or more of the plurality of optical sensors.

20. The apparatus of claim 18, wherein the signal processing circuit is further configured to classify the plurality of read-out signals into at least two signal groups by using position information about the plurality of optical sensors according to a criterion that matches a certain movement pattern of the user and measure the movement component by comparing the at least two signal groups with each other.

* * * * *